United States Patent
Almirante et al.

(10) Patent No.: US 10,093,696 B2
(45) Date of Patent: Oct. 9, 2018

(54) NITRIC OXIDE DONATING CARNOSINE COMPOUNDS

(71) Applicant: NICOX SCIENCE IRELAND, Dublin (IE)

(72) Inventors: Nicoletta Almirante, Milan (IT); Laura Storoni, Cesano Maderno (IT); Elena Bastia, Milan (IT); Stefania Brambilla, Merone (IT); Sergio Romeo, Milan (IT)

(73) Assignee: NICOX SCIENCE IRELAND, Dublin (IE)

( * ) Notice: Subject to any disclaimer, the term of this patent is extended or adjusted under 35 U.S.C. 154(b) by 0 days.

(21) Appl. No.: 15/507,835

(22) PCT Filed: Sep. 2, 2015

(86) PCT No.: PCT/EP2015/070040
§ 371 (c)(1),
(2) Date: Mar. 1, 2017

(87) PCT Pub. No.: WO2016/034619
PCT Pub. Date: Mar. 10, 2016

(65) Prior Publication Data
US 2017/0291920 A1 Oct. 12, 2017

(30) Foreign Application Priority Data
Sep. 4, 2014 (EP) .................... 14183478

(51) Int. Cl.
*A61K 38/00* (2006.01)
*C07K 5/062* (2006.01)
*A61K 38/05* (2006.01)
*A61K 45/06* (2006.01)
*A61K 9/00* (2006.01)

(52) U.S. Cl.
CPC ........ *C07K 5/06026* (2013.01); *A61K 9/0048* (2013.01); *A61K 38/05* (2013.01); *A61K 45/06* (2013.01)

(58) Field of Classification Search
None
See application file for complete search history.

(56) References Cited

U.S. PATENT DOCUMENTS

2011/0245177 A1   10/2011   Babizhayev

FOREIGN PATENT DOCUMENTS

WO   WO 95/10294 A1   4/1995
WO   WO 00/61537 A2   10/2000
WO   WO 2008/095841 A2   8/2008

OTHER PUBLICATIONS

Bertinaria et al., "Carnosine analogues containing No-donor substructures: Synthesis physico-chemical characterization and preliminary pharmacological profile," European Journal of Medicinal Chemistry, 2012, pp. 103-112, vol. 54.
Guiotto et al., "Carnosine and Carnosine-Related Antioxidants: A Review," Current Medicinal Chemistry, Sep. 1, 2005, pp. 2293-2315, vol. 12, No. 20, Bentham Science Publishers, NL.
International Search Report and Written Opinion issued in PCT/EP2015/070040 dated Nov. 4, 2015.
Mincione et al., "Carbonic Anhydrase Inhibitors: 4-Sulfamoyl-benzenecarboxamides and 4-Chloro-3-sulfamoyl-benzenecarboxamides with Strong Topical Antiglaucoma Properties," Bioorganic & Medicinal Chemistry Letters, Jan. 1, 2001, pp. 1787-1791, vol. 11, No. 13, Pergamon, Amsterdam.
Saada et al., "Carbonic Anhydrase Activators: Gold Nanoparticles Coated with Derivatized Histamine, Histidine, and Carnosine Show Enhanced Activatory Effects on Several Mammalian Isoforms," Journal of Medicinal Chemistry, Mar. 10, 2011, pp. 1170-1177, vol. 54, No. 5.
Scozzafava et al., "Carbonic Anhydrase Activators: High Affinity Isozymes I, II, and IV Activators, Incorporating a β-Alanyl-histidine Scaffold," Journal of Medicinal Chemistry, Jan. 17, 2002, pp. 284-291, vol. 45, No. 2, American Chemical Society, US.

*Primary Examiner* — Jeanette M Lieb
(74) *Attorney, Agent, or Firm* — Arent Fox LLP

(57) ABSTRACT

The present invention relates to nitric oxide donor carnosine derivatives having a great efficacy in reducing elevated intraocular pressure, to processes for their preparation and to their use in the treatment and/or prophylaxis of glaucoma and ocular hypertension.

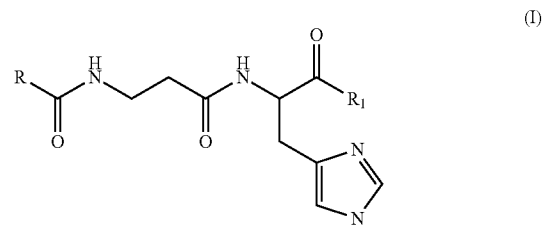

(I)

18 Claims, No Drawings

NITRIC OXIDE DONATING CARNOSINE COMPOUNDS

CROSS-REFERENCE TO RELATED APPLICATIONS

This application is a National Stage entry of International Application No.: PCT/EP2015/070040, filed Sep. 2, 2015, which claims priority to European Patent Application No. 14183478.8, filed Sep. 4, 2014. The disclosure of the priority applications are hereby incorporated in their entirety by reference.

The present invention relates to nitric oxide donating carnosine analogues of formula (I) for the use in the treatment and/or prophylaxis of glaucoma and ocular hypertension.

The present invention also relates to combinations comprising the nitric oxide donor compounds of formula (I) and one or more further active ingredients for the use in the treatment and/or prophylaxis of glaucoma and ocular hypertension.

Glaucoma that includes normotensive and hypertensive glaucoma, is a disease of the eye characterized by a progressive loss of visual field due to irreversible damage to the optic nerve to the point where, if untreated, may result in total blindness. Hypertensive glaucoma occurs when an imbalance in production and drainage of fluid in the eye (aqueous humor) increases eye pressure to unhealthy levels.

Conversely, normotensive glaucoma occurs despite the intraocular pressure is maintained to reasonably low levels. On the basis of its etiology, hypertensive glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Common causes of secondary glaucoma are intraocular tumors, enlarged cataracts, central retinal vein occlusion, trauma to the eye, operative procedures and intraocular hemorrhage.

Normotensive glaucoma is a chronic progressive optic neuropathy resulting in typical optic nerve head changes, retinal nerve fiber layer defects, and characteristic visual field defects. In addition, the chamber angle is open and IOP values within statistical normal limits (lower than 22 mmHg) (Lee et al. 1998; for review, see Hoyng and Kitazawa 2002). There is evidence that treatment of normotensive glaucoma by lowering IOP can slow the glaucomatous process. A reduction of at least 30% in IOP is needed to induce a favorable alteration in this disease.

Elevated intraocular pressure (ocular hypertension) is a common post-surgical complications following ocular surgery such as pars plana vitrectomy, vitreoretinal surgery, retinal detachment surgery, panretinal photocoagulation.

In addition other common causes of elevated intraocular pressure are intraocular inflammation, pupillary block and steroids treatments. In particular intravitreal injections of triamcinolone are associated with elevation of intraocular pressure.

Drug therapies that have proven to be effective for the treatment of glaucoma and the reduction of intraocular pressure include both agents that decrease aqueous humor production and agents that increase the outflow facility, such as beta-blockers, alpha-agonists, cholinergic agents, carbonic anhydrase inhibitors, or prostaglandin analogs.

However, pharmaceutical ocular anti-hypertension approaches have exhibited various undesirable side effects. For example, topical beta-blockers show serious pulmonary side effects, depression, fatigue, confusion, impotence, hair loss, heart failure and bradycardia.

Topical alpha-agonists have a fairly high incidence of allergic or toxic reactions; topical cholinergic agents (miotics) can cause visual side effects.

The side effects associated with oral carbonic anhydrase inhibitors include fatigue, anorexia, depression, paresthesias and serum electrolyte abnormalities (The Merck Manual of Diagnosis and Therapy, Seventeenth Edition, M. H. Beers and R. Berkow Editors, Sec. 8, Ch. 100).

Finally, the topical prostaglandin analogs (bimatoprost, latanoprost, travoprost, tafluprost and unoprostone) used in the treatment of glaucoma can produce ocular side effects, such as increased pigmentation of the iris, ocular irritation, conjunctival hyperaemia, iritis, uveitis and macular oedema (Martindale, Thirty-third edition, p. 1445).

It is known that in the eye, nitric oxide (NO) has an important role in certain physiological processes, e.g. regulation of aqueous humor dynamics, vascular tone, retinal neurotransmission, retinal ganglion cell death by apoptosis, phototransduction and ocular immunological responses, however, the overproduction of NO is involved in several diseases of the eye. Takahata K et al. Invest Ophthalmol Vis Sci. 2003 April; 44(4):1760-6. Kashiwagi K et al. Curr Eye Res. 2001 October; 23(4):233-9.

U.S. Pat. No. 4,590,207 discloses ophthalmic solution containing isosorbide mononitrate as an active ingredient for treating and/or preventing intraocular hypertension and glaucoma.

US patent application 2002/0168424 discloses the use of a mixture of a nitric oxide (NO) donor such as nitrovasodilators like minoxidil, nitroglycerin, L-arginine, isosorbide dinitrate, or nitroprusside, and a cyclic guanosine 3',5'-monophosphate (cGMP) specific phosphodiesterase type 5 (PDE5) inhibitor such as sildenafil citrate for treating glaucoma or ocular hypertension. According to the disclosed combinations promotes systemic vascular relaxation, enhanced blood flow to the optic nerve, dilation of the trabecular meshwork, the Schlemm's canal and uveoscleral outflow channel tissues, enhanced aqueous humor drainage and thus lowered intraocular pressure (IOP) in mammalian eye.

WO 95/10294 discloses that N-acetylcarnosine is a prodrug for L-carnosine, and proposes a topical medicament containing N-acetylcarnosine useful in the prevention and therapy of cataract.

US 2011/0245177 discloses the use of ophthalmic compositions containing N-acetylcarnosine in combination with a cellulose compound for treating eye diseases. In particular US 2011/0245177 reports the results of a clinical study showing that there was a tendency towards improvement of glare sensitivity in adults patients upon topical application of a formulation containing N-acetylcarnosine and carboxymethylcellulose.

Gasco A. et al., (European Journal of Medicinal Chemistry, 54 (2012) 103-112) discloses a class of carnosine amide derivatives containing NO-donating substructures. The document disclose the antioxidant and vasodilator activities of these compounds and it suggests their use as potential tools for treating chronic vascular and neurodegenerative diseases in which NO-bioavailability is reduced.

WO2000/061537 discloses derivatives of drugs containing an NO-donating carnosine structure. These compounds have antioxidant proprieties and can be used to treat the pathologies associated with oxidative stress and/or endothelial dysfunction.

WO2008/095841 discloses nitrooxy derivatives of amino acids as NO donors for the treatment of various diseases. No pharmacological data are reported.

However, the above-mentioned therapies for glaucoma and ocular hypertension are far from satisfactory in view of the potency of the ocular hypotensive effect and the duration of action and currently there are no drugs based on nitric oxide donors that are approved for treating glaucoma or ocular hypertension.

Therefore there is still an unmet need for compounds which are able to efficiently treat glaucoma and ocular hypertension.

Therefore, the technical problem underlying the present invention is to provide effective therapeutic agents for the use in the treatment and/or prophylaxis of hypertensive glaucoma, normotensive glaucoma and ocular hypertension.

It has now been found that the nitric oxide donating carnosine analogues of the present invention are highly effective in reducing intraocular pressure.

The present invention provides nitric oxide donors having a great efficacy in reducing intraocular pressure and better pharmacological proprieties than those of nitric oxide donors described in the art.

The present invention relates to carnosine analogues of formula (I) or a pharmaceutically acceptable salt or stereoisomer thereof:

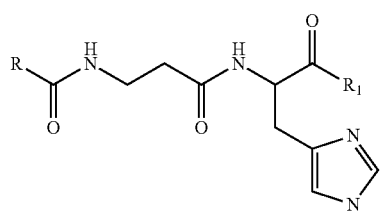

(I)

wherein R is:

—(Y)—(CH$_2$)$_n$—[CH(ONO$_2$)]$_p$—CH$_2$—ONO$_2$   1)

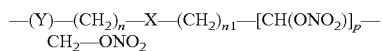

—(Y)—(CH$_2$)$_n$—X—(CH$_2$)$_{n1}$—[CH(ONO$_2$)]$_p$—CH$_2$—ONO$_2$   2)

wherein:
Y is O, NH or a covalent single bond, preferably Y is a covalent single bond;
n is an integer from 1 to 10, preferably 1 to 4; with the proviso that in formula 2) when Y is O or NH, then n is not 1;
n$_1$ is an integer from 1 to 10, preferably 1 to 4;
p is 0 or 1;
X is O, NH or S, preferably O;
R$_1$ is OH, —OR$_2$, —NH$_2$, —NHR$_2$, wherein R$_2$ is (C$_1$-C$_{10}$) linear or branched alkyl, preferably R$_1$ is OH, or —OR$_2$, wherein R$_2$ is (C$_1$-C$_4$) linear alkyl, preferably —CH$_3$.

Carnosine is the dipeptide beta-alanine-histidine that contains the optically active amino acid, histidine, therefore carnosine exists as L-carnosine (beta-alanyl-L-histidine) and D-carnosine (beta-alanyl-D-histidine).

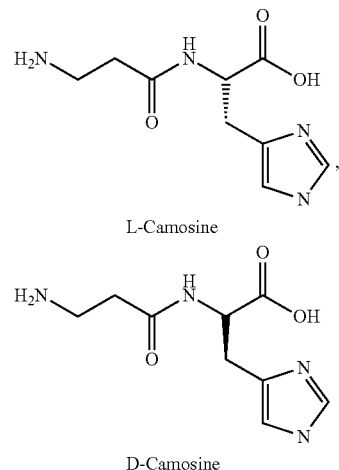

Formula (I) is accordingly intended to embrace analogues of L-carnosine (beta-alanyl-L-histidine) and of D-carnosine (beta-alanyl-D-histidine).

Preferred carnosine analogues of formula (I) provided by the present invention are L-carnosine derivatives and pharmaceutically acceptable salt thereof.

The present invention provides the salts of those compounds of formula (I) that have salt-forming groups, especially the salts of the compounds having a carboxylic group or a basic nitrogen atom. The salts are especially physiologically tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic organic acids (e.g. acetic, trifluoroacetic, p-toluenesulphonic acid).

The present invention encompasses all the possible stereoisomers, as well as their racemic or optically active mixtures.

A (C$_1$-C$_{10}$) linear or branched alkyl is preferably a C$_1$-C$_4$ alkyl group, e.g. methyl, ethyl, propyl, isopropyl, butyl, sec-butyl or tert-butyl, in particular methyl or ethyl.

An embodiment of the present invention provides compounds of formula (I) as above defined wherein R, n, n$_1$, p and R$_1$ are as above defined, Y is a covalent single bond and X is O.

Another embodiment of the present invention provides compounds of formula (I) as above defined wherein R, n, n$_1$, p, and X are as above defined, Y is a covalent single bond and R$_1$ is OH.

Another embodiment of the present invention provides compounds of formula (I) as above defined wherein R, n, n$_1$, p, and X are as above defined, Y is a covalent single bond and R$_1$ is —OCH$_3$.

Another embodiment of the present invention provides compounds of formula (I) as above defined wherein R is —(Y)—(CH$_2$)$_n$—[CH(ONO$_2$)]$_p$—CH$_2$—ONO$_2$ wherein Y is a covalent single bond, n, n$_1$, p are as above defined, R$_1$ is OH.

Another embodiment of the present invention provides compounds of formula (I) as above defined wherein R is —(Y)—(CH$_2$)$_n$—X—(CH$_2$)$_{n1}$—[CH(ONO$_2$)]$_p$—CH$_2$—ONO$_2$ wherein Y is a covalent single bond, X is O, n, n$_1$, p are as above defined, R$_1$ is OH.

Another embodiment of the present invention provides compounds of formula (I) as above defined wherein R is 1) —(Y)—(CH$_2$)$_n$—[CH(ONO$_2$)]$_p$—CH$_2$—ONO$_2$ wherein Y is a covalent single bond, n, n$_1$, p are as above defined, R$_1$ is —OCH$_3$.

Another embodiment of the present invention provides compounds of formula (I) as above defined wherein R is —(Y)—(CH$_2$)$_n$—X—(CH$_2$)$_{n1}$—[CH(ONO$_2$)]$_p$—CH$_2$—ONO$_2$ wherein Y is a covalent single bond, X is O, n, n$_1$, p are as above defined, R$_1$ is —OCH$_3$.

Preferred compounds of formula (I) of the present invention are selected from the group consisting of:

(1)
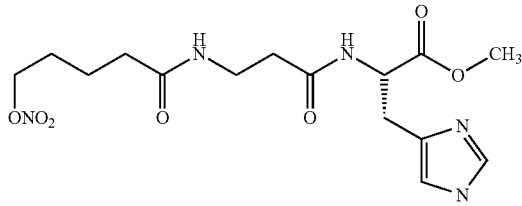

(2)
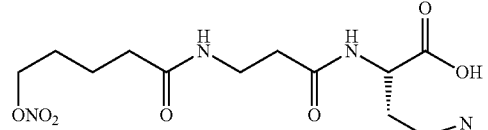

(3)
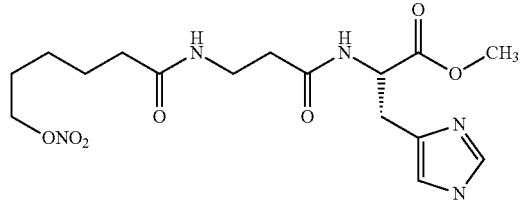

(4)
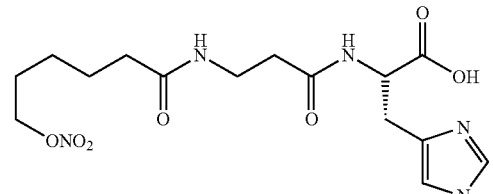

(5)
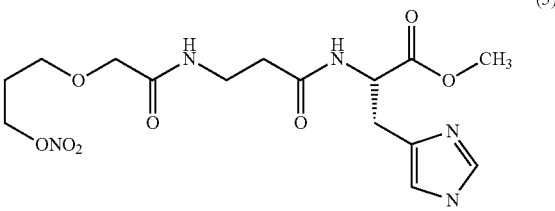

(6)
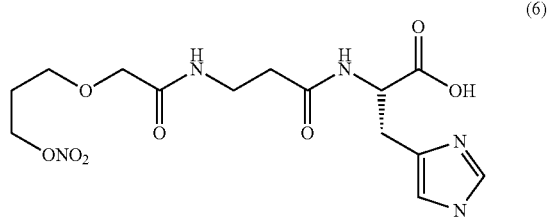

(7)
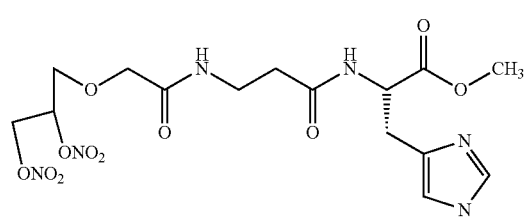

(8)
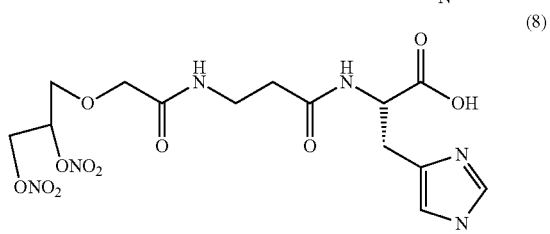

(9)
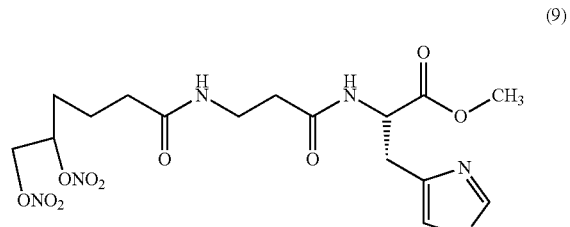

(10)
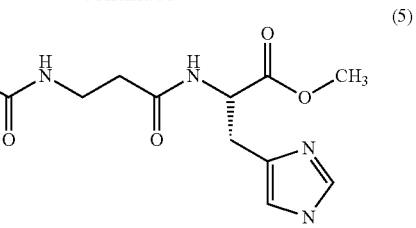

The present invention also relates to compounds of formula (I) or stereoisomers thereof for use in the treatment and/or prophylaxis of hypertensive glaucoma, normotensive glaucoma and ocular hypertension.

Ocular hypertension includes high intraocular pressure conditions resulting from orbital edema, intraocular inflammation, pupillary block and steroids treatments and complications following ocular surgery.

The present inventions also relates to compositions comprising a nitric oxide donor of formula (I) as above defined in combination with one or more further active ingredients selected from the group consisting of alpha adrenergic agonist, beta blocker, carbonic anhydrase inhibitor, prostaglandin analogs, non-steroidal anti-inflammatory drugs, steroidal anti-inflammatory drugs.

Examples of suitable alpha adrenergic agonist are brimonidine, apraclonidine, clonidine.

Examples of suitable beta blocker are timolol, carteolol, betaxolol, levobunolol.

Examples of suitable carbonic anhydrase inhibitor are dorzolamide, acetazolamide, brinzolamide, dorzolamide, dichlorphenamide, methazolamide.

Examples of suitable prostaglandin analogs are bimatoprost, latanoprost, travoprost, unoprostone and tafluprost.

Examples of non-steroidal anti-inflammatory drugs are bromfenac, flurbiprofen, naproxen, ketoprofen.

Examples of steroidal anti-inflammatory drugs are dexamethasone, fluocinolone acetonide, fluocinolone, triamcinolone acetonide, triamcinolone, budesonide, prednisolone.

Another embodiment of the present invention is the compositions as above defined for use in the treatment and/or prophylaxis of hypertensive glaucoma, normotensive glaucoma and ocular hypertension.

Another embodiment of the present invention provides pharmaceutical formulation for topical, periocular or intraocular administration comprising at least a nitric oxide donor of formula (I) and at least an ophthalmically acceptable component and/or ophthalmically acceptable vehicle.

Another embodiment of the present invention provides pharmaceutical formulation for topical, periocular or intraocular administration comprising at least a nitric oxide donor of formula (I) one or more further active ingredients selected from the group consisting of alpha adrenergic agonist, beta blocker, carbonic anhydrase inhibitor, prostaglandin analogs, non-steroidal anti-inflammatory drugs, steroidal anti-inflammatory drugs and at least an ophthalmically acceptable component and/or ophthalmically acceptable vehicle.

Examples of formulations adapted for topical administration to the eye include, but are not limited to, eye drops, eye ointment and ophthalmic gel.

The preferred route of administration of the compounds and compositions of the present invention is topical.

An "ophthalmically acceptable" component refers to a component which will not cause any significant ocular damage or ocular discomfort at the intended concentration and over the time of intended use. Solubilizers and stabilizers should be non-reactive. An "ophthalmically acceptable vehicle" refers to any substance or combination of substances which are non-reactive with the compounds and suitable for administration to a patient.

The nitric oxide donors of the present invention will generally be contained in the topical, periocular, or intraocular formulations contemplated herein in an amount of from about 0.001 to about 10.0% weight/volume. Preferred concentrations will range from about 0.1 to about 5.0% w/v.

General Synthesis

A) Compound of Formula (I) Wherein $R_1$ is —$OR_2$, —$NH_2$, —$NHR_2$

The compounds of formula (I) as above defined, wherein $R_1$ is —$OR_2$, —$NH_2$, —$NHR_2$, $R_2$ is as above defined, R is as above defined, Y is a single covalent bond, X is O or S, n, $n_1$ and p are as above defined, can be prepared by reacting a compound of formula (II), wherein R1 is as above defined:

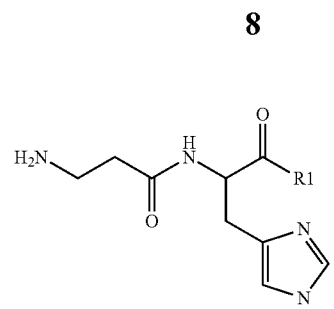

with a compound of formula (IIIa,b),

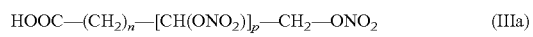

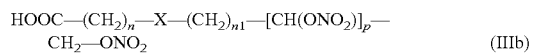

wherein n, $n_1$, X and p are as above defined, in the presence of a coupling reagent such as DCC, EDC, HBTU, HATU, and a catalytic amount of DMAP or Sc(OTf)$_3$ in an aprotic/non polar solvent such as THF, DMF or CH$_2$Cl$_2$, at a temperature ranging from −80° C. to 60° C. as depicted in Scheme 1; or alternatively ii) with a compound of formula (IVa,b):

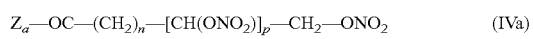

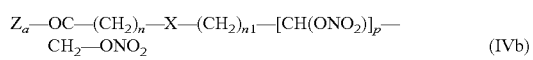

wherein n, $n_1$, p, and X are as above defined and $Z_a$ is an activating group selected from $N_3$, F, Cl, Br, or a group of formula ($Z_{a1}$) or ($Z_{a2}$),

preferably $Z_a$ is Cl or ($Z_{a1}$), in presence of a base such as DMAP, pyridine or triethylamine or K$_2$CO$_3$, Cs$_2$CO$_3$ in an aprotic/non polar solvent such as THF, DMF or CH$_2$Cl$_2$, at a temperature ranging from −80° C. to 60° C. as depicted in Scheme 1:

Scheme 1

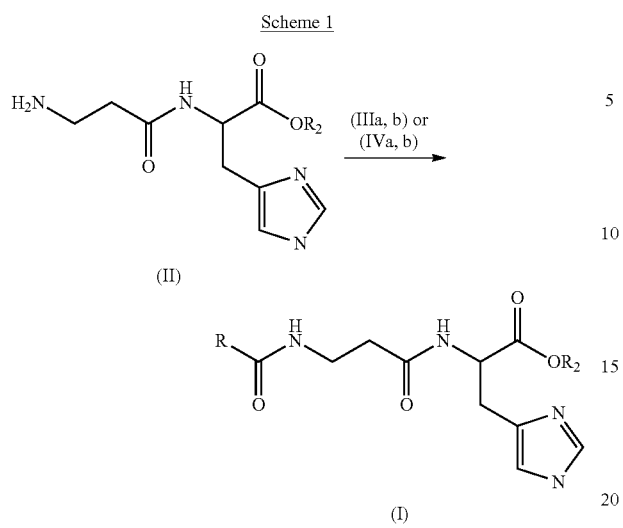

Compounds of formula (II) are known in the art or can be prepared with known methods from carnosine.

Compounds of formula (IIIa,b) are known in the art or can be prepared from known compounds by known methods such as for example from the corresponding alcohols of formula (Va,b), wherein n, $n_1$, p and X are as above defined, by oxidation with known agents such as TEMPO.

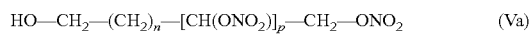

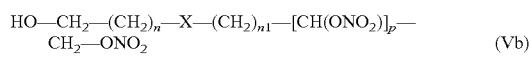

Compounds of formula (IVa,b) can be prepared from compounds of formula (IIIa,b) by methods well known in the art. Alternatively compounds of formula (IVa,b) wherein $Z_a$ is a group of formula $(Z_{a1})$ or $(Z_{a2})$ and p is 0 can be prepared by nitrating the corresponding compounds of formula (VIa,b):

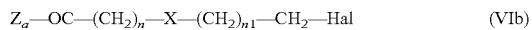

wherein $Z_a$ is a group of formula $(Z_{a1})$ or $(Z_{a2})$, n, n1, and X are as above defined and Hal is a halogen atom, such as Cl or Br, with $AgNO_3$, under reaction conditions well known in the art.

Compounds of formula (VIa,b) can be easily prepared by esterification from known compounds.

Compounds of formula (Va,b) are known in the art or can be prepared from known compounds by known methods.

The compounds of formula (I) as above defined wherein $R_1$ is —$OR_2$, —$NH_2$, —$NHR_2$, wherein $R_2$ is as above defined, R is as above defined, Y is a single covalent bond, X is NH, n, $n_1$ and p are as above defined can be prepared by reacting a compound of formula (II) as above defined, with:

i) a compound of formula (IIIc),

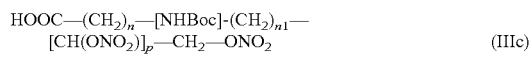

wherein n, n1 and p are as above defined; Boc is the t-butyloxycarbonyl protecting group; in the presence of a coupling reagent such as DCC, EDC, HBTU, HATU, and a catalytic amount of DMAP or Sc(OTf)$_3$ in an aprotic/non polar solvent such as THF, DMF or CH$_2$Cl$_2$ at temperature ranging from −80° C. to 60° C.; or ii) a compound of formula (IVc),

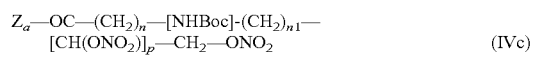

wherein n, n1, p, $Z_a$ and Boc are as above defined;
in the presence of a base such as DMAP, pyridine or triethylamine or $K_2CO_3$, $Cs_2CO_3$ in an aprotic/non polar solvent such as THF, DMF or CH$_2$Cl$_2$ at temperature ranging from −80° C. to 60° C.;
to obtain a compound of formula (VIIa)

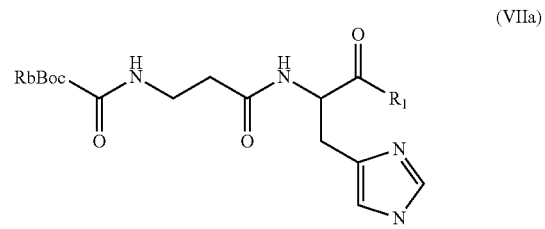

wherein RbBoc is —(CH$_2$)$_n$—[NHBoc]-(CH$_2$)$_{n1}$—[CH(ONO$_2$)]$_p$—CH$_2$—ONO$_2$, n, $n_1$, p and Boc are as above defined and eventually removing the Boc protecting group by methods known in the art such as acid treatment.

Compounds of formula (IVc) can be prepared from compounds of formula (IIIc) by methods known in the art. Compounds (IIIc) are known in the art or can be prepared by known compounds with known methods.

The compounds of formula (I) as above defined wherein $R_1$ is —$OR_2$, —NH, —$NHR_2$ wherein $R_2$ is as above defined, R is as above defined, Y is O, X is O or S, n, $n_1$, p are as above defined, can be prepared by reacting compounds (II), as above defined, with compounds of formula (VIIIa,b):

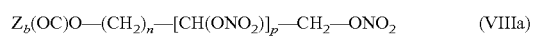

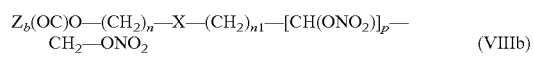

wherein n, $n_1$, X and p are as above defined; $Z_b$ is Cl or is a group of formula $(Z_{a1})$ or $(Z_{a2})$, in presence of a base such as DMAP, pyridine or triethylamine or $K_2CO_3$, $Cs_2CO_3$ in an aprotic/non polar solvent such as THF, DMF or CH$_2$Cl$_2$ or at temperature ranging from −80° C. to 60° C., as known for carbamate formation.

Compounds (VIIIa,b) are known in the art or can be prepared from known compounds by known methods such as for example by reacting the corresponding alcohols of formula (Va,b) as above defined, wherein n, $n_1$, p and X are as above defined, with phosgene, triphosgene or p-nitrophenylcarbonate or N,N'-Disuccinimidyl carbonate.

The compounds of formula (I) as above defined wherein $R_1$ is —$OR_2$, —NH, —$NR_2$ wherein $R_2$ is as above defined, R is as above defined, Y is O, X is NH, n, $n_1$ and p are as above defined, can be prepared by reacting a compound of formula (II) as above defined with a compound of formula (VIIIc),

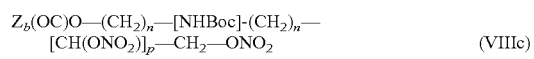

wherein n, Boc, $n_1$, p and $Z_b$ are as above defined; in the presence of a base such as DMAP, pyridine or triethylamine or $K_2CO_3$, $Cs_2CO_3$ in an aprotic/non polar solvent such as THF, DMF or CH$_2$Cl$_2$, at a temperature ranging from −80° C. to 60° C., according to known methods for the formation of carbamates, eventually removing the Boc protecting group from the obtained compound of formula (VIIb):

(VIIb)

wherein $R_1$ is as above defined and RdBoc is —O—$(CH_2)_n$—[NHBoc]-$(CH_2)_{n1}$—[CH$(ONO_2)$]$_p$—$CH_2$—$ONO_2$, according to methods known in the art.

Compounds (VIIIc) are known in the art or can be prepared from known compounds by known methods such as for example by reacting the corresponding alcohols of formula (IXc):

HO—$(CH_2)_n$—[NHBoc]-$(CH_2)_{n1}$—[CH$(ONO_2)$]$_p$—$CH_2$—$ONO_2$ (IXc)

wherein n, Boc, $n_1$ and p are as above defined, with phosgene, triphosgene or p-nitrophenylcarbonate or N,N'-Disuccinimidyl carbonate.

Compounds (IXc) are known in the art or can be prepared from known compounds by known methods.

The compounds of formula (I) as above defined wherein $R_1$ is —$OR_2$, —$NH_2$, —$NHR_2$ wherein $R_2$ is as above defined, R is as above defined, Y is NH, X is O or S;
can be prepared by reacting compounds of formula (II), as above defined, with compounds of formula (Xa,b), $Z_c$(OC)NH—$(CH_2)_n$—[CH$(ONO_2)$]$_p$—$CH_2$—$ONO_2$ (Xa)

$Z_c$(OC)ONH—$(CH_2)_n$—[X]—$(CH_2)_{n1}$—[CH$(ONO_2)$]$_p$—$CH_2$—$ONO_2$ (Xb)

Wherein n, n1, X and p are as above defined; $Z_c$ is Cl or is a group of formula ($Z_{a1}$) as above defined, or a group of formula ($Z_{a3}$):

($Z_{a3}$)

in the presence of a base such as DMAP, pyridine or triethylamine or $K_2CO_3$, $Cs_2CO_3$ in an aprotic/non polar solvent such as THF, DMF or $CH_2Cl_2$, at a temperature ranging from −80° C. to 60° C., according to the methods known in the art for ureas formation.

Compounds ($X_{a-b}$) are prepared by reacting the corresponding amine (XIa,b):

$H_2N$—$(CH_2)_n$—[CH$(ONO_2)$]$_p$—$CH_2$—$ONO_2$ (XIa)

$H_2N$—$(CH_2)_n$—X—$(CH_2)_n$—[CH$(ONO_2)$]$_p$—$CH_2$—$ONO_2$ (XIb)

with phosgene, triphosgene or p-nitrophenyl chloroformate or phenyl chloroformate according to methods known in the art.

Compounds (XIa,b) are known in the art or can easily be prepared from known products by known methods.

The compounds of formula (I) as above defined wherein $R_1$ is —$OR_2$, —$NH_2$, —$NHR_2$ wherein $R_2$ is as above defined, Y is NH, X is NH, n, $n_1$ and p are as above defined can be prepared by reacting compounds (II), as above defined with compounds of formula (Xc):

$Z_c$(OC)ONH—$(CH_2)_n$—[NHBoc]-$(CH_2)_{n1}$—[CH$(ONO_2)$]$_p$—$CH_2$—$ONO_2$ (Xc)

wherein n, $n_1$, Boc, p and $Z_c$ is as above defined in the presence of a base such as DMAP, pyridine or triethylamine or $K_2CO_3$, $Cs_2CO_3$ in an aprotic/non polar solvent such as THF, DMF or $CH_2Cl_2$ at a temperature ranging from −80° C. to 60° C., according to methods known in the art for ureas formation, eventually removing the Boc protecting group from the obtained compound (VIIc):

(VII$_c$)

wherein RfBoc is —NH—$(CH_2)_n$—[NHBoc]-$(CH_2)_{n1}$—[CH$(ONO_2)$]$_p$—$CH_2$—$ONO_2$ Compounds of formula (Xe) can be prepared from the corresponding amine (XIc):

$H_2N$—$(CH_2)_n$—[NHBoc]-$(CH_2)_{n1}$—[CH$(ONO_2)$]$_p$—$CH_2$—$ONO_2$ (XIc)

by reacting with phosgene, triphosgene or p-nitrophenyl chloroformate or phenyl chloroformate according to known methods.

Compounds (XIc) are known in the art or can easily be prepared from known products by known methods.

Alternatively the compounds of formula (I) wherein $R_1$ is —$OR_2$, wherein $R_2$ is as above defined, R is as above defined, Y is as above defined, X is O or S, n, $n_1$ and p are as above defined can be obtained according to the below Scheme 2:

(Scheme 2)

wherein R and $R_2$ are as above defined, A is —OH, Cl or $Z_{a1}$ as above defined.

When A is —OH the reaction is carried out in the presence of a coupling reagent such as DCC, EDC, HBTU, HATU, and of a catalytic amount of DMAP or $Sc(OTf)_3$ in an aprotic/non polar solvent such as THF, DMF or $CH_2Cl_2$ at a temperature ranging from −80° C. to 60° C.

When A is Cl or $Z_{a1}$, the reaction is carried out in the presence of a base such as DMAP, pyridine or triethylamine or $K_2CO_3$, $Cs_2CO_3$ in an aprotic/non polar solvent such as THF, DMF or $CH_2Cl_2$ at a temperature ranging from −80° C. to 60° C.

The compounds of formula (XIII) are commercially available or known in the art.

The compounds of formula (XII) as above defined, wherein A is Cl, or ($Z_{a1}$) can be prepared by known methods from the compounds of formula (XII) as above defined wherein A is OH.

The compounds of formula (XII), wherein A is OH and R is as above defined, can be prepared according to the following scheme 3:

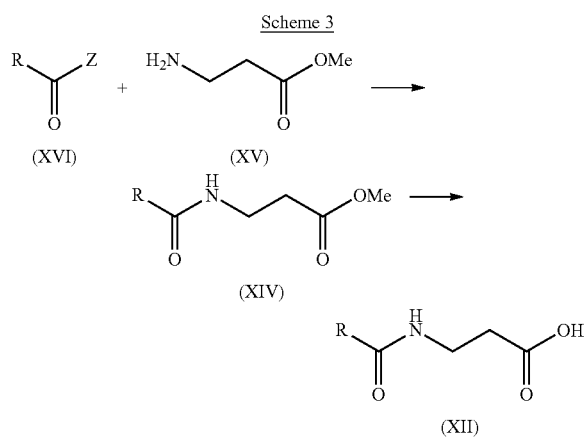

by basic hydrolysis of the corresponding compounds of formula (XIV) which in turn can be prepared, by methods known in the art for the formation of amides, carbamates or ureas, by reacting commercially available compounds of formula (XV) with compounds of formula (XVI) wherein:

Z is $Z_a$, as above defined, when Y in the radical R is a single covalent bond;
Z is $Z_b$, as above defined, when Y in the radical R, is O;
Z is $Z_c$, as above defined, when Y in the radical R, is NH.

Compound of formula (XVI) are equivalent to compounds (IVa,b), (VIIIa,b), (Xa,b) already described.

Alternatively the compounds of formula (I) as above defined wherein $R_1$ is —$OR_2$, wherein $R_2$ is as above defined, R is:

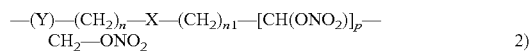

wherein Y is as above defined, X is NH, n, $n_1$ and p are as above defined, can be prepared from the corresponding compounds of formulae VII, wherein RBoc is RbBoc, RdBoc, RfBoc as above defined by removing the Boc protecting group as described above.

The compounds of formulae VII as above defined can be prepared according to Scheme 4, by reacting a commercially available compound of formula (XII) wherein $R_2$ is as above defined with the compounds of formula (XVII) wherein A is —OH, Cl or $Z_{a1}$ as above defined:

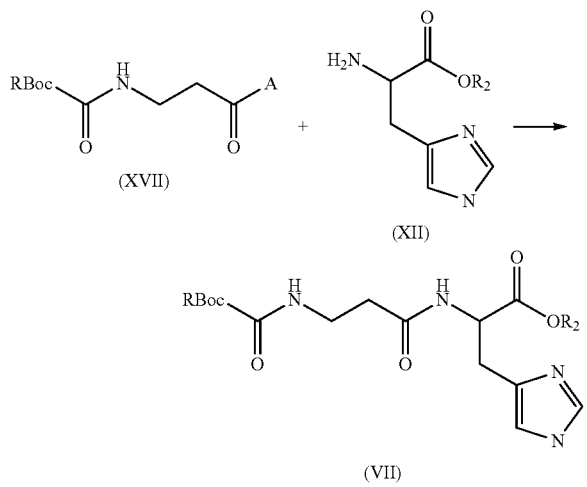

Compounds (XVII) wherein A is Cl, or ($Z_{a1}$) can be prepared by known methods from Compounds (XVII) wherein A is OH.

Compounds (XVII) wherein A is OH can be prepared according to the following Scheme 5, by basic hydrolysis of corresponding compounds (XVIII) which in turn can be prepared by methods known in the art for amides, carbamates or ureas formation, by reacting a commercially available compound of formula (XV) with compounds of formula (XIX) wherein:

Z is $Z_a$, as above defined, when Y in the radical R is a single covalent bond;
Z is $Z_b$, as above defined, when Y in the radical R, is O;
Z is $Z_c$, as above defined, when Y in the radical R, is NH.

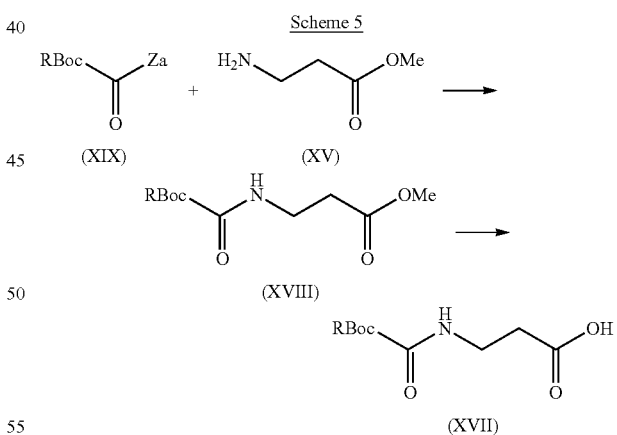

Compounds of formula (XIX) are equivalent to compounds (IVc), (VIIIc), (Xc) already described.

B) The compounds of formula (I) wherein $R_1$ is —OH

The compounds of formula (I) as above defined wherein $R_1$ is —OH, R, Y, X, n, $n_1$ and p are as above defined can be prepared by reacting the corresponding compounds of formula (I), (VIIa), (VIIb) or (VIIc), wherein $R_1$ is $OR_2$, with NaOH or KOH in aqueous medium with the methods known in the art for esters hydrolysis, eventually removing the Boc protecting group when present.

EXAMPLES

Glossary

ACN Acetonitrile
Cy Cyclohexane
DCC Dicyclohexylcarbodiimide
DCM dichloromethane
DMAP 4-dimethylaminopyridine
DMF N,N-Dimethylformamide
DMSO Dimethyl sulfoxide
EDC*HCl N-(3-Dimethylaminopropyl)-N'-ethylcarbodiimide hydrochloride
EtOAc Ethyl Acetate
iPrOH 2-Propanol
MTBE tert-Butyl methyl ether
RT room temperature
TEA Triethylamine
TFA Trifluoroacetic acid

Example 1

Synthesis of (S)-methyl 3-(1H-imidazol-4-yl)-2-(3-(5-(nitrooxy)pentanamido) propanamido)propanoate (Compound (1))

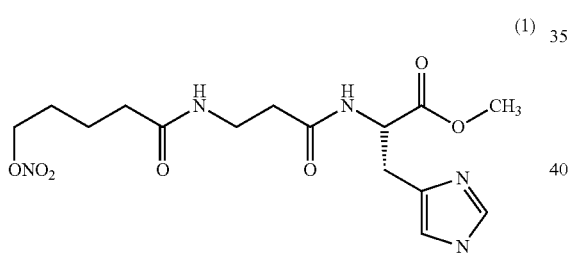

Step 1: Synthesis of 4-nitrophenyl 5-bromopentanoate

To a solution of 5-bromovaleric acid (5 g, 27.6 mmol) and DCC (5.7 g, 27.6 mmol) in DCM (200 ml), p-nitrophenol (4.23 g, 30.4 mmol) was added portionwise. The mixture was stirred overnight at RT, then precipitate was filtered off and the solvent was removed under reduced pressure. The crude was purified by flash chromatography (EtOAc in cyclohexane from 5% to 50%) affording 7.1 g of desired compound (Yield: 85%)

MS: m/z=303 [M+H]+

TLC: (Cy/EtOAc 9:1) Rf=0.40

Step 2: Synthesis of 4-nitrophenyl 5-(nitrooxy)pentanoate

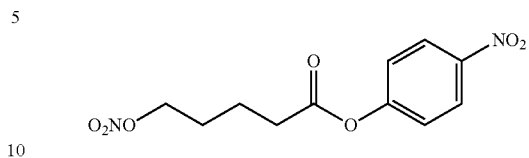

To a solution of 4-nitrophenyl 5-bromopentanoate (5 g, 16.6 mmol) in CH₃CN (145 ml), kept in the dark, AgNO₃ (2 g, 12 mmol) was added. The mixture was heated at 80° C. After 15 minutes, AgNO₃ (1 g, 6 mmol) was added and after 1 hour, the last portion of AgNO₃ (1.25 g, 7.3 mmol) was added. The reaction was left under stirring for 2 hours.

Then, the salts were filtered off and the solvent concentrated. EtOAc was added to the residue and the salts filtered off again. The solution was concentrated and the residue purified by flash chromatography (DCM 100%) affording 4.12 g of the desired compound (Yield: 87%).

MS: m/z=285 [M+H]+

TLC: (DCM 100%) Rf=0.30

Step 3: Synthesis of methyl (2S)-2-[(3-aminopropanoyl)amino]-3-(4H-imidazol-4-yl)propanoate hydrochloride

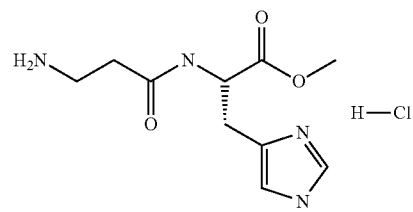

To a suspension of L-Carnosine (3 g, 13.2 mmol) in dry MeOH (100 ml) cooled at 0° C., SOCl₂ (1.13 ml, 15.6 mmol) was added dropwise and the mixture was stirred 10 minutes. The solution was then refluxed for 1 h and, after cooling to RT and the solvent was removed under reduced pressure. The product was triturated in DCM/MTBE 1/1 for 2 hours at rt, filtered and dried in vacuum to give the desired product in quantitative yield.

MS: m/z=241 [M+H]+

Step 4: Synthesis of (S)-methyl 3-(1H-imidazol-4-yl)-2-(3-(5-(nitrooxy)pentanamido) propanamido) propanoate (Corresponding to Compound (1))

To a solution of 4-nitrophenyl 5-(nitrooxy)pentanoate (2 g, 7.04 mmol) and methyl (2S)-2-[(3-aminopropanoyl) amino]-3-(4H-imidazol-4-yl)propanoate hydrochloride (2.2 g, 7.04 mmol) in DMF (16 ml) cooled at 0° C., TEA (3.2 ml, 21.12 mmol) was added dropwise. The solution was stirred for 15 minutes and DMAP (84 mg, 0.7 mmol) was added. The solution was stirred at RT overnight, the solvent removed under reduced pressure. The residue was purified by flash chromatography (85:15 DCM:MeOH-1% NH₄OH)

affording 1.8 g of (S)-methyl 3-(1H-imidazol-4-yl)-2-(3-(5-(nitrooxy)pentanamido) propanamido)propanoate (Yield: 66%).

MS: m/z=386 [M+H]+

TLC: (DCM/MeOH/NH$_4$OH 79:20:1) R$_f$=0.55

$^1$H NMR (300 MHz, DMSO) δ 8.96 (s, 1H), 8.41 (d, J=7.9, 1H), 7.82 (t, J=5.5, 1H), 7.38 (s, 1H), 4.67-4.53 (m, 1H), 4.49 (t, J=6.2, 2H), 3.63 (s, 3H), 3.22-2.90 (m, 4H), 2.31-2.18 (m, 2H), 2.06 (t, J=7.0, 2H), 1.70-1.43 (m, 4H).

Example 2

Synthesis of (S)-3-(1H-imidazol-4-yl)-2-(3-(5-(nitrooxy)pentanamido) propanamido)propanoic acid 2,2,2-trifluoroacetate (Compound (2a) that Corresponds to Compound (2) as 2,2,2-trifluoroacetate) and (S)-3-(1H-imidazol-4-yl)-2-(3-(5-(nitrooxy) pentanamido) propanamido)propanoic acid acetate (Compound (2b) that Corresponds to Compound (2) as Acetate)

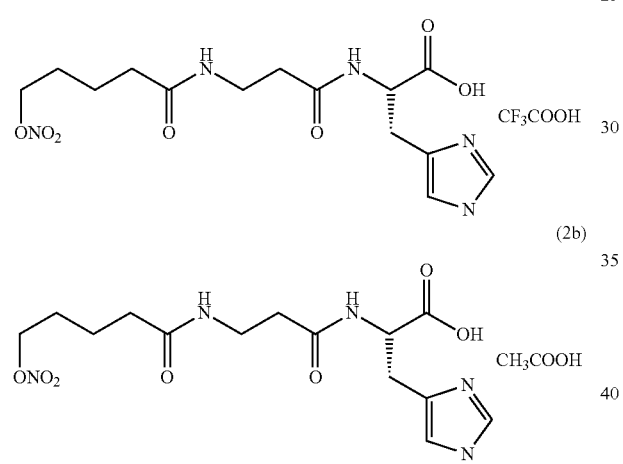

To a solution of compounds (1) (described in Example 1) (0.3 g, 0.78 mmol) in H$_2$O/Dioxane (1:3) cooled at 0° C., KOH 2.5M solution (0.9 ml, 1.44 mmol) was added dropwise. The solution was stirred for 1 hour. When the reaction was completed the solvent was removed under reduce pressure. The residue was dissolved in DCM and iPrOH (1%) and was purified by flash chromatography (60:40 DCM:iPrOH-2% Acetic acid) affording 89 mg of the title compound as acetate (2b).

MS: m/z=372 [M+H]+

TLC: (DCM/iPrOH/AceticAcid 60:38:2) Rf=0.20

In order to obtain the trifluoro acetate derivative (2a), a solution of compounds (1) (described in Example 1) (0.3 g, 0.78 mmol) in H$_2$O/Dioxane (1:3) cooled at 0° C., was treated with KOH 2.5M solution (0.9 ml, 1.44 mmol), added dropwise. The solution was stirred for 1 hour. When the reaction was completed the solvent was removed under reduce pressure. The residue was dissolved in DCM and iPrOH (1%) and was purified by preparative HPLC:

Column: Kinetex AXIA 21.2×250 mm 5 micron C18

A: H2O 0.05% TFA

B: ACN 0.05% TFA

Flow: 16 ml/min

Gradient:

95% A to 50% A in 10 min.

50% A to 95% A in 2 min.

Detection: UV @ 210 nm

Affording 0.100 mg of the title compound (2a)

$^1$H NMR (300 MHz, DMSO) δ 8.96 (s, 1H), 8.26 (m, 1H), 7.82 (m, 1H), 7.33 (s, 1H), 4.71-4.35 (m, 3H), 3.32-2.81 (m, 4H), 2.36-2.12 (m, 2H), 2.12-1.90 (m, 2H), 1.81-1.28 (m, 4H).

Example 3

Synthesis of (S)-methyl 3-(1H-imidazol-4-yl)-2-(3-(6-(nitrooxy)hexanamido) propanamido) 2,2,2-trifluoroacetate (Compound (3a) that Corresponds to Compound (3) as 2,2,2-trifluoroacetate)

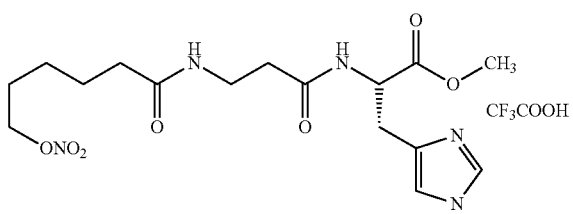

Step 1: Synthesis of 4-nitrophenyl 6-bromoexanoate

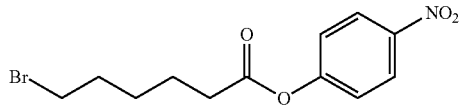 [SMILES: O=C(CCCCCBr)Oc1ccc([N+](=O)[O-])cc1]

To a solution of 6-Bromohexanoic acid and DCC in DCM, p-nitrophenol was added portion wise. The mixture was stirred overnight at RT. Progress was checked by TLC (Cy/AcOEt 5:5). Once the reaction was complete, the mixture was filtered, evaporated and purified by flash chromatography (Gradient: Cy/AcOEt 5% to 50%), yielding 4-nitrophenyl 6-bromoexanoate (1.301 g, 80.3%).

$^1$H NMR (300 MHz, CDCl$_3$) δ 8.33-8.21 (m, 2H), 7.33-7.23 (m, 2H), 3.45 (t, J=6.6 Hz, 2H), 2.64 (t, J=7.4 Hz, 2H), 1.93 (dt, J=14.6, 6.8 Hz, 2H), 1.86-1.74 (m, 2H), 1.65-1.54 (m, 2H).

Step 2: Synthesis of 4-nitrophenyl 6-(nitrooxy)hexanoate

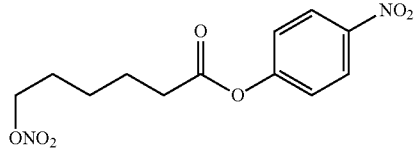

To a solution of 4-nitrophenyl 6-bromohexanoate (1.301 g, 4.12 mmol) in CH$_3$CN (30 ml), kept in the dark, AgNO$_3$ (840.85 mg, 4.95 mmol) was added. The mixture was refluxed overnight. Then, the salts were filtered off and the solvent concentrated. EtOAc was added to the residue and the salts filtered off again. The solution was concentrated and the residue purified by flash chromatography (DCM 100%) affording 1.2 g of the 4-nitrophenyl 6-(nitrooxy) hexanoate (Yield: 97.6%).

$^1$H NMR (300 MHz, CDCl$_3$) δ 8.28 (d, J=9.1 Hz, 2H), 7.28 (d, J=9.5 Hz, 2H), 4.49 (t, J=6.4 Hz, 2H), 2.64 (t, J=7.3 Hz, 2H), 1.82 (q, J=7.7 Hz, 4H), 1.56 (td, J=8.7, 4.1 Hz, 2H).

Step 3: Synthesis of (S)-methyl 3-(1H-imidazol-4-yl)-2-(3-(6-(nitrooxy)hexanamido) propanamido) propanoate 2,2,2-trifluoroacetate To a solution of 4-nitrophenyl 6-(nitrooxy)hexanoate (Step 2) (656.1 g, 2.2 mmol) and methyl-(2S)-2-[(3-amino-propanoyl)amino]-3-(4H-imidazol-4-yl)propanoate hydrochloride (obtained in Example 1, Step 3) (0.538.7, 2.2 mmol) in DMF (16 ml) cooled at 0° C., TEA (0.306 ml, 2.2 mmol) was added dropwise. The solution was stirred at RT overnight, the solvent removed under reduce pressure. The crude was then solubilized in water and purified by reverse phase HPLC. (Phase A: H$_2$O+TFA 0.1%; Phase B: MeOH+TFA 0.1%; linear gradient t=0: A 95%, B 5%, t=20': 100% B, t=25' 100% B; flow: 14 ml/min) affording 399 mg of the title compound (Yield: 36.5%).

$^1$H NMR (300 MHz, DMSO) δ 8.98 (s, 1H), 8.42 (d, J=7.7, 1H), 7.80 (t, J=5.7, 1H), 7.39 (s, 1H), 4.68-4.53 (m, 1H), 4.48 (t, J=6.6, 2H), 3.62 (s, 3H), 3.20-2.89 (m, 6H), 2.33-2.13 (m, 2H), 2.02 (t, J=7.3, 2H), 1.72-1.55 (m, 2H), 1.55-1.38 (m, 2H), 1.36-1.18 (m, 2H).

Example 4

Synthesis of (S)-3-(1H-imidazol-4-yl)-2-(3-(6-(nitrooxy)hexanamido)propanamido) propanoic acid 2,2,2-trifluoroacetate (Compound (4a) that Corresponds to Compound (4) as 2,2,2-trifluoroacetate)

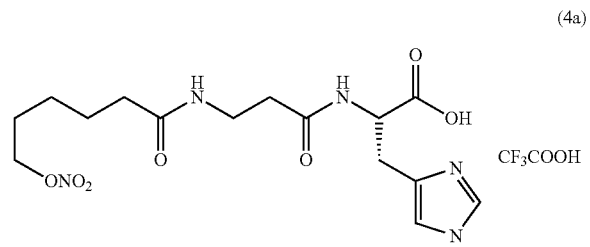

(4a)

To a solution of (S)-methyl 3-(1H-imidazol-4-yl)-2-(3-(6-(nitrooxy)hexanamido) propanamido)propanoate (Example 3) (150 mg, 0.302 mmol) in Dioxane/H$_2$O (3:1) cooled to 0° C., a solution of KOH (2.5N, 041 ml)) was added dropwise. The solution was left reacting for 3.5 h at room temperature. The solution was then cooled to 0° C. acidified with HCl conc. to pH=2 and the dioxane evaporated at reduced pressure. The crude was then purified with reverse phase HPLC. The crude was then purified with reverse phase HPLC. (Phase A: H$_2$O+TFA 0.1%; Phase B: MeOH+TFA 0.1%; linear gradient t=-0: A 95%, B 5%, t=20': 100% B, t=-25' 100% B; flow: 14 ml/min) yielding the title compound (76 mg, 52%).

$^1$H NMR (300 MHz, DMSO) δ 8.97 (s, 1H), 8.29 (d, J=8.1, 1H), 7.77 (t, J=5.7, 1H), 7.36 (s, 1H), 4.65-4.40 (m, 3H), 3.26-2.83 (m, 4H), 2.35-2.11 (m, 2H), 2.02 (t, J=7.3, 2H), 1.73-1.54 (m, 2H), 1.54-1.37 (m, 2H), 1.37-1.16 (m, 2H).

Example 5

Synthesis of (S)-methyl 3-(1H-imidazol-4-yl)-2-(3-(2-(2-(nitrooxy)ethoxy)acetamido) propanamido) propanoate 2,2,2-trifluoroacetate (Compound (5a) that Corresponds to Compound (5) as 2,2,2-trifluoroacetate)

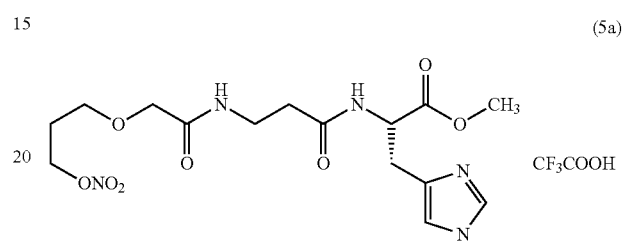

(5a)

Step 1: Synthesis of 2-(2-hydroxyethoxy)ethyl nitrate

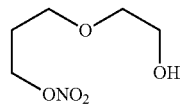

Ethylene glycol (4 g, 37.7 mmol) in DCM (200 ml) was cooled to −30° C. and a mixture of HNO$_3$ (1.6 ml, 37.7 mmol) in Acetic anhydride (10.7 ml) was added dropwise under vigorous stirring. The mixture was left reacting at −30° C. for 2 h. The crude was poured on ice and diluted with AcOEt. The two phases were separated, and the organic phase washed with NaHCO$_3$, H$_2$O and brine. The organic phase was dried over Na$_2$SO$_4$ anhydrous, filtered and concentrated to afford reddish oil, containing 2-(2-hydroxyethoxy)ethyl nitrate (2.28 g, 40%) that was used without any further purification for the next step.

$^1$H NMR (300 MHz, CDCl$_3$) δ 4.69-4.59 (m, 2H), 3.85-3.66 (m, 4H), 3.61 (dd, J=5.2, 3.8 Hz, 2H).

Step 2: Synthesis of 2-(2-(nitrooxy)ethoxy)acetic acid

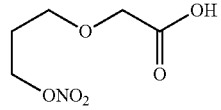

To a solution of 2-(2-hydroxyethoxy)ethyl nitrate (Step 1) (1 g, 6.6 mmol) in acetone (25 ml), cooled at 0° C., a saturated solution of NaHCO$_3$ (8 ml), NaBr (276.9 mg, 2.64 mmol) and TEMPO (206 mg, 1.32 mmol) were added. Trichloroisocyanuric acid (3.1 g, 13.2 mmol) was added portion wise. The reaction was allowed to reach RT and stirred for 3 h The mixture was then cooled to 0° C. and 10 ml of isopropanol were slowly added. The mixture was stirred at 0° C. for 30 minutes and the precipitate was filtered off and the solvent concentrated. The residue was basified with NaOH 2M (pH=12) and washed twice with EtOAc. To the aqueous phase HCl conc. was added until pH=2-3 and then extracted with EtOAc (5×). The combined organic phases were dried over $Na_2SO_4$ and concentrated to afford the title compound (875 mg, 80.3%) as pale yellow oil.

$^1$H NMR (300 MHz, $CDCl_3$) δ 4.71-4.62 (m, 2H), 4.20 (s, 2H), 3.94-3.84 (m, 2H).

Step 3: Synthesis of 4-nitrophenyl 2-(2-(nitrooxy)ethoxy)acetate

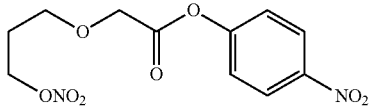

To a solution of 2-(2-(nitrooxy)ethoxy)acetic acid (Step 2) (875 mg, 5.3 mmol) and DCC (1.093 g, 5.3 mmol) in DCM, p-nitrophenol (811 mg, 5.83 mmol) was added portionwise. The mixture was stirred overnight at RT. Then the mixture was filtered, evaporated and purified by flash chromatography (Gradient: Cy/AcOEt 5% to 50%) yielding the title compound (1.43 g, 94.3%).

Step 4: Synthesis of (S)-methyl 3-(1H-imidazol-4-yl)-2-(3-(2-(2-(nitrooxy)ethoxy) acetamido)propanamido)propanoate 2,2,2-trifluoroacetate A solution of 4-nitrophenyl 2-(2-(nitrooxy)ethoxy)acetate (251.8 mg, 0.88 mmol) (Step 3) and methyl (2S)-2-[(3-aminopropanoyl)amino]-3-(4H-imidazol-4-yl)propanoate hydrochloride (211.42 mg, 0.88 mmol) (prepared as described in Example 1, Step 3) was cooled to 0° C. and N-methyl-morpholine (0.097 ml, 0.88 mmol) was added dropwise until pH 7-8. The solution was stirred overnight at RT. The crude was then evaporated, solubilized in water and purified with reverse phase HPLC (Phase A: $H_2O$+TFA 0.1%; Phase B: MeOH+TFA 0.1%; linear gradient t=0: A 95%, B 5%, t=20': 100% B, t=25' 100% B; flow: 14 ml/min) to afford the title compound (186 mg, 43.5%).

$^1$H NMR (300 MHz, DMSO) δ 8.95 (s, 1H), 8.44 (d, J=7.8, 1H), 7.73 (t, J=5.7, 1H), 7.38 (s, 1H), 4.82-4.49 (m, 3H), 3.86 (s, 2H), 3.81-3.69 (m, 2H), 3.58 (s, J=21.8, 3H), 3.30-3.17 (m, 2H), 3.17-2.90 (m, 2H), 2.39-2.16 (m, 2H).

Example 6

Synthesis of (S)-3-(1H-imidazol-4-yl)-2-(3-(2-(2-(nitrooxy)ethoxy)acetamido) propanamido)propanoic acid 2,2,2-trifluoroacetate (Compound (6a) that Corresponds to Compound (6) as 2,2,2-trifluoroacetate)

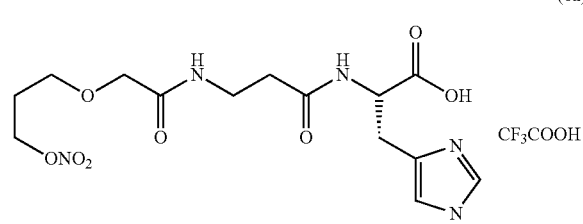

(6a)

The title compound was obtained from (S)-methyl 3-(1H-imidazol-4-yl)-2-(3-(2-(2-(nitrooxy)ethoxy)acetamido) propanamido)propanoate (Example 5) following the same procedure described in Examples 2 and 4.

The crude was purified with reverse phase HPLC (Phase A: $H_2O$+TFA 0.1%; Phase B: MeOH+TFA 0.1%; linear gradient t=0: A 95%, B 5%, t=20': 100% B, t=25' 100% B; flow: 14 ml/min) affording the title compound (70 mg, 47.6%).

$^1$H NMR (300 MHz, DMSO) δ 8.95 (s, 1H), 8.34-8.31 (m, 1H), 7.76-7.72 (s, 1H), 7.38 (s, 1H), 4.67 (m, 2H), 4.53 (m, 1H), 3.86 (s, 2H), 3.73 (m, 2H), 3.23 (m, 2H), 3.12 (m, 1H), 2.95 (m, 1H), 2.27 (m, 2H).

Example 7

Synthesis of (S)-methyl 2-(3-((S)-5,6-bis(nitrooxy) hexanamido)propanamido)-3-(1H-imidazol-4-yl) propanoate (Corresponding to Compound (9), (S) Isomer)

(9)

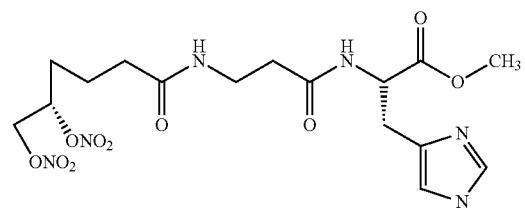

Step 1: Synthesis of Hex-5-enyl-4-nitrobenzoate

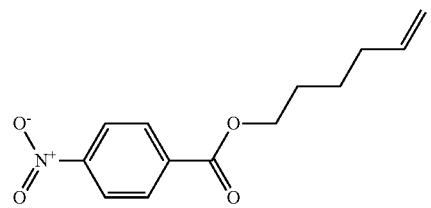 [SMILES: C=CCCCCOC(=O)c1ccc([N+](=O)[O-])cc1]

To a stirred solution of hex-5-enol (21.25 g, 200 mmol) and 4-nitrobenzoyl chloride (37.11 g, 200 mmol) in dichloromethane (300 mL) at 0° C., triethylamine (28 mL, 200 mmol) was added. The reaction was stirred at RT for 4 h and washed with water, HCl 1M, water and brine. The solvent was removed under reduced pressure to give a crude oil which was treated with n-hexane to give a solid that was filtered off. The mother liquor was evaporated to give the title compound as yellow oil (41 g, 82%).

MS: m/z=250 [M+H]$^+$

TLC: DCM 100% $R_f$=0.4

Step 2: Synthesis of (5S)-5,6-dihydroxyhexyl 4-nitrobenzoate

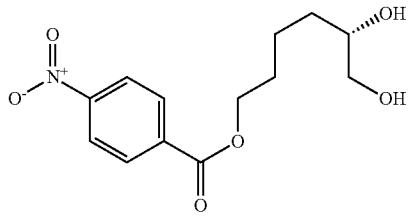 [SMILES: O=C(OCCCC[C@H](O)CO)c1ccc([N+](=O)[O-])cc1]

A stirred solution of AD-Mix α (50 g) in a mixture tBuOH/H₂O (227 mL each) was stirred for 10 min at room temperature and then cooled to 4° C. After 15 min, hex-5-enyl 4-nitrobenzoate (Step 1) (8.8 g, 35.5 mmol) was added and the reaction stirred overnight at 4° C. Then ethyl acetate (200 mL) was added and followed by careful addition of sodium metabisulfite (12 g). The reaction was left for 30 min at 4° C. and then treated with water (200 mL). The organic layer was extracted and the aqueous phase extracted twice with ethyl acetate (2×100 mL). The combined organic phases were washed with water and brine, dried over sodium sulfate, evaporated to give a white solid (9.7 g, 97%).

The residue was dissolved in diethylether (100 mL) and stirred overnight to give the title compound as white solid (8.1 g, 84%).

MS: 284 [M+H]⁺

TLC: (DCM/MeOH-0.5%) $R_f$=0.36

Step 3: Synthesis of (5S)-5,6-bis(nitrooxy)hexyl 4-nitrobenzoate

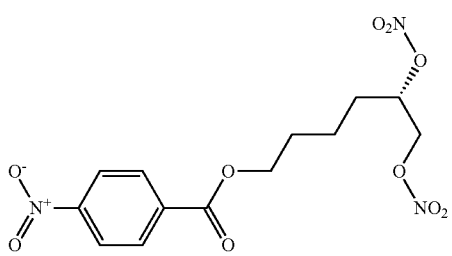 [SMILES: O=C(OCCCC[C@@H](CO[N+](=O)[O-])O[N+](=O)[O-])c1ccc([N+](=O)[O-])cc1]

To a stirred solution of fuming nitric acid (3.6 mL, 88 mmol, 5 eq) in dichloromethane (3 mL) at 0° C., was added acetic anhydride (13.7 mL) and after 10 mins of stirring, a solution of (5S)-5,6-dihydroxyhexyl 4-nitrobenzoate (Step 2) (5 g, 17.6 mmol) in dichloromethane (2 mL) was added and the reaction stirred at this temperature for 60 min. The crude mixture was then poured on ice and the organic layer extracted, washed with water, brine, dried over sodium sulfate, evaporated to give the title compound as pale yellow oil (6.4 g, 99%). The residue obtained was used in the next step without further purification.

MS: 374 [M+H]⁺

TLC: (DCM 100%) $R_f$=0.37

Step 4: Synthesis of (2S)-6-hydroxy-2-(nitrooxy)hexyl nitrate

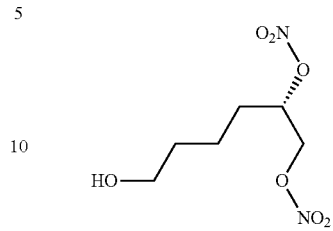

To a stirred solution of (5S)-5,6-bis(nitrooxy)hexyl 4-nitrobenzoate (Step 3) (7.4 g, 19.82 mmol) in a 1/1 mixture of ethanol/THF (33 mL of each) at 0° C., a 2 M sodium hydroxide solution (19.8 mL, 2 eq) was added and the reaction was stirred for 2 h. The reaction was diluted with ethyl acetate and water (100 mL of each) and extracted. The organic layer was successively washed with water and brine, dried over sodium sulfate and evaporated. The oily residue was purified by column chromatography (gradient system from 4/6 ethyl acetate/Cy to 60/40 ethyl acetate/Cy) to give the title compound as colorless oil (4.1 g, 92%).

TLC: (EtOAc/Cy-50%) $R_f$=0.31

Step 5: Synthesis of (5S)-5,6-bis(nitrooxy)hexanoic acid

To a solution of (2S)-6-hydroxy-2-(nitrooxy)hexyl nitrate (Step 4) (3 g, 13.4 mmol) and Sodium periodate (8.4 g, 40.2 mmol) in CHCl₃, ACN, H₂O (1:1:1), ruthenium (IV) oxide (180 mg, 1.34 mmol) was added. The mixture was stirred overnight at RT, the precipitate was filtered off and the solvent was removed under reduced pressure. The residue was dissolved in DCM, washed with water, dried with MgSO₄, filtered and concentrated under reduced pressure. The crude was purified by flash chromatography (EtOAc in cyclohexane from 5% to 50%) affording 2.4 g of (5S)-5,6-bis(nitrooxy)hexanoic acid (Yield: 75%)

TLC: (DCM/MeOH-0.5%) $R_f$=0.34

Step 6: Synthesis of (S)-methyl 2-(3-((S)-5,6-bis(nitrooxy)hexanamido)propanamido)-3-(1H-imidazol-4-yl)propanoate (Corresponding to Compound (9), (S) Isomer)

To a solution of (5S)-5,6-bis(nitrooxy)hexanoic acid (2.4 g, 10 mmol) and methyl-(2S)-2-[(3-aminopropanoyl)amino]-3-(4H-imidazol-4-yl)-propanoate (Example 1, Step 3) (3.1 g, 10 mmol) in DMF (40 ml) cooled at 0° C., TEA (5.5 ml, 40 mmol) was added dropwise. The solution was stirred for 15 minutes EDC*HCl (1.91 g, 10 mmol) and DMAP (1.22 g, 10 mmol) were added. The solution was stirred at RT overnight, the solvent removed under reduced pressure. The residue was purified by flash chromatography (80:20 DCM:MeOH-1% NH₄OH) affording 1.9 g of the (S)-methyl 2-(3-((S)-5,6-bis(nitrooxy)hexanamido)propanamido)-3-(1H-imidazol-4-yl)propanoate (Yield: 41%).

MS: m/z=461 [M+H]⁺

TLC: (DCM/MeOH/NH₄OH 79:20:1) $R_f$=0.40

¹H NMR (600 MHz, cd3od) δ 7.61 (s, 1H), 6.88 (s, 1H), 5.42 (m, 1H), 4.94-4.85 (m, 1H), 4.72-4.64 (m, 1H), 4.64-

4.54 (m, 1H), 3.72 (s, 3H), 3.49-3.35 (m, 2H), 3.16-3.07 (m, 1H), 3.07-2.97 (m, 1H), 2.50-2.35 (m, 2H), 2.30-2.19 (m, 2H), 1.82-1.66 (m, 4H).

Example 8

Synthesis of (S)-2-(3-((S)-5,6-bis(nitrooxy)hexanamido)propanamido)-3-(1H-imidazol-4-yl)propanoic acid 2,2,2-trifluoroacetate (Compound (10a) that Corresponds to Compound (10), (S) Isomer, 2,2,2-trifluoroacetate) and (S)-2-(3-((S)-5,6-bis(nitrooxy)hexanamido)propanamido)-3-(1H-imidazol-4-yl) propanoic acid acetate (Compound (10b) that Corresponds to Compound (10), (S) Isomer, Acetate)

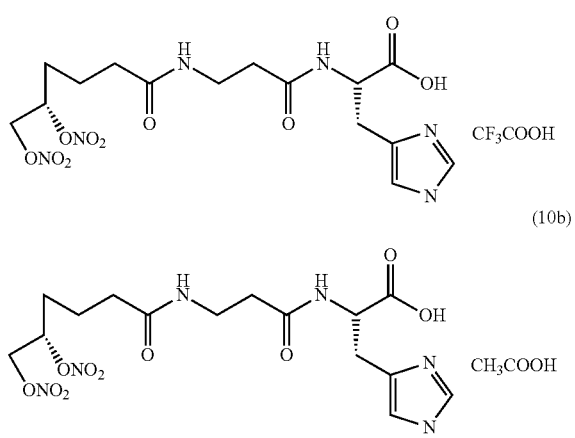

To a solution of (S)-methyl 2-(3-((S)-5,6-bis(nitrooxy)hexanamido)propanamido)-3-(1H-imidazol-4-yl)propanoate (Example 7) (0.6 g, 1.3 mmol) in $H_2O$/Dioxane (1:3) cooled at 0° C., KOH 2.5M solution (1.5 ml, 3.9 mmol) was added dropwise. The solution was stirred for 1 hour and the solvent was removed under reduced pressure. The crude was dissolved in DCM/water then HCl was added until pH of 1-2 and the solvent was removed under reduced pressure. The residue was solubilized in DCM and iPrOH (1%) and was purified by flash chromatography (50:40 DCM:iPrOH-2% Acetic acid) affording 400 mg of (S)-2-(3-((S)-5,6-bis(nitrooxy)hexanamido)propanamido)-3-(1H-imidazol-4-yl) propanoic acid acetate (10b) (Yield: 69%).

From 150 mg of (10b) 110 mg of (10a) were obtained by preparative HPLC according to the following conditions:
Column: Kinetex AXIA 21.2×250 mm 5 micron C18
A: $H_2O$ 0.05% TFA
B: ACN 0.05% TFA
Flow: 16 ml/min.
Gradient:
from 95% A to 50% A in 10 min.
from 50% A to 95% A in 2 min.
iso 95% A for 3 min.
Detection UV @ 210 nm
MS: m/z=447 [M+H]+
$^1$H NMR (600 MHz, d2o) δ 8.49 (s, 1H), 7.18 (s, 1H), 5.42-5.21 (m, 2H), 4.82-4.72 (m, 1H), 4.68-4.58 (m, 1H), 4.57-4.47 (m, 1H), 3.34-3.14 (m, 2H), 3.12-2.96 (m, 1H), 2.43-2.27 (m, 2H), 2.18-2.08 (m, 2H), 1.68-1.51 (m, 4H).

Example 9

Intraocular Pressure (IOP) Lowering Activity in Hypertonic Saline-Induced IOP Increase in Rabbits The present study evaluated the intraocular pressure lowering effect of single applications of two compounds of the inventions (compound (1a) and compound (4a)) and two reference compounds at the same concentrations and in rabbits with induced IOP increase.

Tested Compounds

Compound (1a) is (S)-methyl-3-(1H-imidazol-4-yl)-2-(3-(5-(nitrooxy)pentanamido) propanamido)propanoate hydrochloride and was prepared from compound (1) obtained in Example 1 and hydrochloric acid by known methods. Compound (4a): was prepared as described in (Example 4)

Timolol and 5-ISMN were tested as reference compounds

Timolol is a drug commonly used for the treatment of glaucoma and ocular hypertension. Isosorbide mononitrate (5-ISMN) is a commonly used nitric oxide donor drug.

Adult male New Zealand White rabbits weighting 1.8-2.0 Kg were used in the experiments.

The transient increase in IOP was induced by the injection of 0.1 ml of hypertonic saline solution (5%) into the vitreous bilaterally (Krauss et al., 2011, Orihashi et al., 2005).

IOP was measured using a Tono-Pen XL prior to hypertonic saline injection (basal) and at 30, 60, 120 and 240 min thereafter. Vehicle (5% cremophor-EL; 0.3% DMSO; 0.2 mg/ml Benzalkonium chloride in PBS pH 6.0) or compound (1.0%) was instilled as eye drops immediately after hypertonic saline injection. Eyes were randomly assigned to different treatment groups. Vehicle and compounds were directly instilled into the conjunctiva pocket at the desired doses. One drop of 0.4% oxybuprocaine hydrochloride (Novesine, Sandoz) was instilled in each eye immediately before each set of pressure measurements.

Results are reported in Table 1 and they are expressed as IOP change (at 60, 120 and 240 minutes following topical administration) versus vehicle and versus IOP at basal before hypertonic saline injection. Single application of compounds (1a) and (4a) resulted in a significant IOP reduction compared to ISMN and timolol.

The experiment results showed that, 4 hours after instillation the compounds of the invention maintained their ocular hypotensive activity and the IOP-lowering effect in the groups treated with the compounds of the invention is higher than in the groups treated with timolol and 5-ISMN, demonstrating prolonged IOP-lowering effect of the compounds of the invention with respect to the reference compounds.

The experimental results revealed that a potent ocular hypotensive effect and a prolonged action were obtained by using the compounds of the invention.

TABLE 1

Intraocular pressure (IOP) lowering activity in hypertonic saline-induced IOP increase in rabbits

| Test Compound (conc. 1%) | IOP change (mmHg) | | |
| --- | --- | --- | --- |
| | 60 minutes | 120 minutes | 240 minutes |
| Compound (1a) | −11.4 ± 0.8 | −12.9 ± 0.4 | −7.4 ± 0.5 |
| Compound (4a) | −7.6 ± 1.6 | −9.0 ± 1.2 | −5.3 ± 0.6 |
| ISMN | −0.7 ± 2.9 | −6.6 ± 1.8 | −1.2 ± 1.3 |
| Timolol | −5.7 ± 1.4 | −8.4 ± 1.2 | 0.2 ± 1.2 |

Example 10

Intraocular Pressure (IOP) Lowering Activity in Ocular Normotensive New Zealand White Rabbits The present study evaluated the long lasting intraocular pressure lowering effect of single application of two compounds of the inventions (compound (1a) and compound (4a)) with respect to a prior art compound, in an ocular normotensive animal model (rabbit) at the same concentrations.

Tested Compounds

Compound (1a) is (S)-methyl-3-(1H-imidazol-4-yl)-2-(3-(5-(nitrooxy) pentanamido) propanamido)propanoate hydrochloride and was prepared from compound (1) obtained in Example 1 and hydrochloric acid by known methods.

Compound (4a): was prepared as described in (Example 4)

The prior art compound is (R)-3-((S)-2-(3-aminopropanamido)-3-(1H-imidazol-4-yl)propanamido)propane-1,2-diyl dinitrate 2,2,2-trifluoroacetate (reference compound) and it is disclosed in M. Bertinaria et al., European Journal of Medicinal Chemistry, 54(2012) 103-112.

Adult male New Zealand White (NZW) rabbits weighting 1.8-2.0 Kg were used in the experiments.

IOP was measured using a pneumatonometer 30 CLASSIC™ before topical application (basal) and at different time points (30, 60, 120, 240 and 300 min) thereafter. Vehicle (5% cremophor-EL; 0.3% DMSO; 0.2 mg/ml bac in PBS pH 6.0) or compound of the invention were instilled as eye drops into the conjunctiva pocket. Eyes were randomly assigned to different treatment groups. One drop of 0.4% oxybuprocaine hydrochloride (Novesine, Sandoz) was instilled in each eye immediately before each set of pressure measurements. Results are reported in Table 2 and they are expressed as IOP change (at 60, 120, 180 and 240 minutes following topical administration) versus vehicle and versus IOP at basal.

Single application of compound (1a) and compound (4a) results in a significantly longer IOP reduction as compared to the reference compound.

The experiment results revealed that the compounds of the invention showed a higher and prolonged IOP-lowering effect with respect to the reference compound.

TABLE 2

Intraocular pressure (IOP) lowering activity in ocular normotensive rabbits

| Test Compound (1%) | IOP change (mmHg) | | | |
|---|---|---|---|---|
| | 60 minutes | 120 minutes | 180 minutes | 240 minutes |
| Compound (1a) | −1.2 ± 1.0 | −1.5 ± 0.9 | −1.9 ± 0.9 | −1.7 ± 1.2 |
| Compound (4a) | −1.6 ± 0.4 | −1.5 ± 0.6 | −1.4 ± 0.6 | −0.9 ± 0.6 |
| Ref. compound | −0.8 ± 0.6 | −0.3 ± 0.4 | −0.2 ± 0.4 | −0.05 ± 0.6 |

Example 11

Intraocular Pressure (IOP) Lowering Activity

The intraocular pressure lowering effect and the duration of the effect of a single application of the compound (9) were assessed in a transient ocular hypertensive rabbit model and in an ocular normotensive rabbit model respectively.

Tested Compound

Compound (9): (S)-methyl 2-(3-((S)-5,6-bis(nitrooxy) hexanamido)propanamido)-3-(1H-imidazol-4-yl)propanoate; the compound was prepared as described in Example 7.

Hypertonic Saline-Induced IOP Increase Rabbit Model

Adult male New Zealand White rabbits weighting 1.8-2.0 Kg were used in the experiments.

The transient increase in IOP was induced by the injection of 0.1 ml of hypertonic saline solution (5%) into the vitreous bilaterally (Krauss et al., 2011, Orihashi et al., 2005).

IOP was measured using a Tono-Pen XL prior to hypertonic saline injection (basal) and at 30, 60, 120 and 240 min thereafter. Vehicle (5% cremophor-EL; 0.3% DMSO; 0.2 mg/ml Benzalkonium chloride in PBS pH 6.0) or compound (9) (1.0%) was instilled as eye drops immediately after hypertonic saline injection. Eyes were randomly assigned to different treatment groups. Vehicle and compound (9) were directly instilled into the conjunctiva pocket at the desired doses. One drop of 0.4% oxybuprocaine hydrochloride (Novesine, Sandoz) was instilled in each eye immediately before each set of pressure measurements.

Experimental data are reported in Table 3 and they are expressed as IOP change (at 60, 120 and 240 minutes following topical administration) versus vehicle and versus IOP at basal before hypertonic saline injection Ocular Normotensive Rabbit Model Adult male New Zealand White (NZW) rabbits weighting 1.8-2.0 Kg were used in the experiments.

IOP was measured using a pneumatonometer 30 CLASSIC™ before topical application (basal) and at different time points (30, 60, 120, 240 and 300 min) thereafter. Vehicle (5% cremophor-EL; 0.3% DMSO; 0.2 mg/ml bac in PBS pH 6.0) or compound (9) (1%) were instilled as eye drops into the conjunctiva pocket. Eyes were randomly assigned to different treatment groups. One drop of 0.4% oxybuprocaine hydrochloride (Novesine, Sandoz) was instilled in each eye immediately before each set of pressure measurements.

Experimental data are reported in Table 4 and they are expressed as IOP change (at 60, 120, 180 and 240 minutes following topical administration) versus vehicle and versus IOP at basal.

Results

The results of Table 3 show that a single application of compound (9) resulted in a significant IOP reduction. When comparing the IOP reduction effects of compound (9) and of the reference compounds ISMN and timolol a higher IOP reduction was observed after topical application of compound (9) with respect to the IOP reduction induced by the reference compounds ISMN and timolol.

The hypotensive effects of compound (9) and of ISMN and timolol were evaluated using the same transient ocular hypertensive rabbit model, see Example 9, but in different groups of hypertensive rabbits.

The experiment results of the ocular normotensive rabbit model reported in Table 4 show that compound (9) showed a long lasting IOP-lowering effect. When comparing the duration of the IOP reduction effects induced by topical application of compound (9) and of the prior art compound (R)-3-((S)-2-(3-aminopropanamido)-3-(1H-imidazol-4-yl) propanamido)propane-1,2-diyl dinitrate 2,2,2-trifluoroacetate (Reference compound), a higher and prolonged IOP-lowering effect was observed with compound (9) with respect to the Reference compound.

The IOP-lowering effects of compound (9) and of the Reference compound were assessed in the same normotensive rabbit model, see Example 10, but using different groups of hypertensive rabbits.

TABLE 3

Intraocular pressure (IOP) lowering activity of compound (9) in hypertonic saline-induced IOP increase in rabbits

| Test compound (1%) | IOP change (mmHg) | | |
| --- | --- | --- | --- |
| | 60 minutes | 120 minutes | 240 minutes |
| Compound (9) | −7.2 ± 1.0 | −6.4 ± 1.0 | −3.9 ± 0.9 |
| ISMN | −0.7 ± 2.9 | −6.6 ± 1.8 | −1.2 ± 1.3 |
| Timolol | −5.7 ± 1.4 | −8.4 ± 1.2 | 0.2 ± 1.2 |

TABLE 4

Intraocular pressure (IOP) lowering activity of Compound (9) in ocular normotensive rabbits

| Test compound (1%) | IOP change (mmHg) | | | | | |
| --- | --- | --- | --- | --- | --- | --- |
| | 30 minutes | 60 minutes | 120 minutes | 180 minutes | 240 minutes | 300 minutes |
| Compound (9) | −1.6 ± 0.2 | −1.0 ± 0.4 | −1.3 ± 0.2 | −1.3 ± 0.3 | −1.5 ± 0.4 | −1.5 ± 0.4 |
| Ref. compound | −1.0 ± 0.5 | −0.8 ± 0.6 | −0.3 ± 0.4 | −0.2 ± 0.4 | −0.05 ± 0.6 | −0.7 ± 0.4 |

The invention claimed is:

1. A carnosine analogue of formula (I) or a pharmaceutically acceptable salt or stereoisomer thereof:

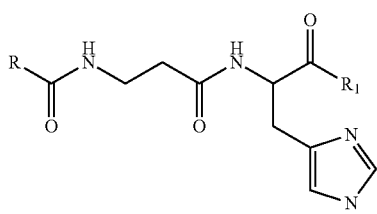
(I)

wherein R is:

1)

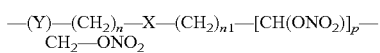
2)

wherein:
Y is O, NH or a covalent single bond;
n is an integer from 1 to 10, preferably 1 to 4; with the proviso that in formula 2) when Y is O or NH, then n is not 1;
$n_1$ is an integer from 1 to 10, preferably 1 to 4;
p is 0 or 1;
X is O, NH or S;
$R_1$ is OH, —$OR_2$, –$NH_2$, —$NHR_2$, wherein $R_2$ is ($C_1$-$C_{10}$) linear or branched alkyl.

2. A carnosine analogue of formula (I) according to claim 1 wherein Y is a covalent single bond and X is O.

3. A carnosine analogue of formula (I) according to claim 1 wherein Y is a covalent single bond and $R_1$ is OH.

4. A carnosine analogue of formula (I) according to claim 3 wherein R is

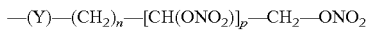
1).

5. A carnosine analogue of formula (I) according to claim 3 wherein R is

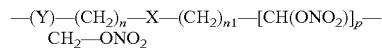
2)

and X is O.

6. A carnosine analogue of formula (I) according to claim 1 wherein Y is a covalent single bond and $R_1$ is —$OCH_3$.

7. A carnosine analogue of formula (I) according to claim 6 wherein R is

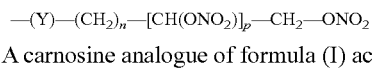
1).

8. A carnosine analogue of formula (I) according to claim 6 wherein R is

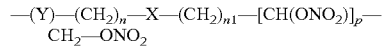
2)

and X is O.

9. A carnosine analogue of formula (I) according to claim 2 wherein p is 0.

10. A carnosine analogue of formula (I) according to claim 2 wherein p is 1.

11. A carnosine analogue according to claim 1 wherein carnosine is L-carnosine.

12. A carnosine analogue of formula (I) according to claim 1 or a pharmaceutically acceptable salt selected from the group consisting of:
(S)-methyl-3-(1H-imidazol-4-yl)-2-(3-(5-(nitrooxy)pentanamido)propanamido) propanoate (compound (1));
(S)-methyl-3-(1H-imidazol-4-yl)-2-(3-(5-(nitrooxy)pentanamido)propanamido) propanoate hydrochloride (compound 1a);
(S)-3-(1H-imidazol-4-yl)-2-(3-(5-(nitrooxy)pentanamido)propanamido)propanoic acid (compound (2));
(S)-3-(1H-imidazol-4-yl)-2-(3-(5-(nitrooxy)pentanamido)propanamido)propanoic acid 2,2,2-trifluoroacetate (compound (2a));
(S)-methyl-3-(1H-imidazol-4-yl)-2-(3-(6-(nitrooxy)hexanamido)propanamido) (compound (3));
(S)-methyl-3-(1H-imidazol-4-yl)-2-(3-(6-(nitrooxy)hexanamido)propanamido) 2,2,2-trifluoroacetate (compound (3a));
(S)-3-(1H-imidazol-4-yl)-2-(3-(6-(nitrooxy)hexanamido) propanamido)propanoic acid (to compound (4));
(S)-3-(1H-imidazol-4-yl)-2-(3-(6-(nitrooxy)hexanamido) propanamido)propanoic acid 2,2,2-trifluoroacetate (compound (4a));
(S)-methyl-3-(1H-imidazol-4-yl)-2-(3-(2-(2-(nitrooxy) ethoxy)acetamido) propanamido)propanoate (compound (5));
(S)-methyl-3-(1H-imidazol-4-yl)-2-(3-(2-(2-(nitrooxy) ethoxy)acetamido) propanamido)propanoate 2,2,2-trifluoroacetate (compound (5a));

(S)-3-(1H-imidazol-4-yl)-2-(3-(2-(2-(nitrooxy)ethoxy) acetamido)propanamido) propanoic acid (compound (6));

(S)-3-(1H-imidazol-4-yl)-2-(3-(2-(2-(nitrooxy)ethoxy) acetamido)propanamido) propanoic acid 2,2,2-trifluoroacetate (compound (6a));

(S)-methyl 2-(3-(2-((S)-2,3-bis(nitrooxy)propoxy)acetamido)propanamido)-3-(1H-imidazol-4-yl)propanoate (compound 7)

(S)-methyl 2-(3-(2-((S)-2,3-bis(nitrooxy)propoxy)acetamido)propanamido)-3-(1H-imidazol-4-yl)propanoate 2,2,2-trifluoroacetate (compound 7a)

(S)-2-(3-(2-((S)-2,3-bis(nitrooxy)propoxy)acetamido) propanamido)-3-(1H-imidazol-4-yl)propanoic acid (compound 8)

(S)-2-(3-(2-((S)-2,3-bis(nitrooxy)propoxy)acetamido) propanamido)-3-(1H-imidazol-4-yl)propanoic acid 2,2,2-trifluoroacetate (compound 8a)

(S)-methyl 2-(3-((5,6-bis(nitrooxy)hexanamido)propanamido)-3-(1H-imidazol-4-yl)propanoate (compound (9));

(S)-methyl 2-(3-((S)-5,6-bis(nitrooxy)hexanamido)propanamido)-3-(1H-imidazol-4-yl)propanoate 2,2,2-trifluoroacetate (compound (9a));

(S)-2-(3-((5,6-bis(nitrooxy)hexanamido)propanamido)-3-(1H-imidazol-4-yl)propanoic acid (compound (10));

(S)-2-(3-((S)-5,6-bis(nitrooxy)hexanamido)propanamido)-3-(1H-imidazol-4-yl)propanoic acid 2,2,2-trifluoroacetate (compound (10a));

(S)-2-(3-((S)-5,6-bis(nitrooxy)hexanamido)propanamido)-3-(1H-imidazol-4-yl)propanoic acid acetate (compound (10b)).

13. A composition comprising a carnosine analogue of formula (I) according to claim 1 and at least a further active ingredient selected from the group consisting of alpha adrenergic agonist, beta blocker, carbonic anhydrase inhibitor, prostaglandin analogs, non-steroidal anti-inflammatory drugs, steroidal anti-inflammatory drugs.

14. A method of treating hypertensive glaucoma, normotensive glaucoma, and/or ocular hypertension, comprising administering to a subject in need thereof a carnosine analogue of formula (I) according to claim 1.

15. A pharmaceutical formulation comprising a carnosine analogue according to claim 12 and an ophthalmically acceptable component and/or ophthalmically acceptable vehicle.

16. A method of treating hypertensive glaucoma, normotensive glaucoma, and/or ocular hypertension, comprising administering to a subject in need thereof a carnosine analogue according to claim 12.

17. Pharmaceutical formulation comprising at least a carnosine analogue of formula (I) according to claim 1 and at least an ophthalmically acceptable component and/or ophthalmically acceptable vehicle.

18. Pharmaceutical formulation comprising at least a composition according to claim 13 and at least an ophthalmically acceptable component and/or ophthalmically acceptable vehicle.

* * * * *